United States Patent [19]

James et al.

[11] Patent Number: 5,503,770

[45] Date of Patent: Apr. 2, 1996

[54] FLUORESCENT COMPOUND SUITABLE FOR USE IN THE DETECTION OF SACCHARIDES

[75] Inventors: Tony James; Saman Sandanayake; Seiji Shinkai, all of Fukuoka, Japan

[73] Assignee: Research Development Corporation of Japan, Saitama, Japan

[21] Appl. No.: 336,236

[22] Filed: Nov. 7, 1994

[30] Foreign Application Priority Data

Nov. 7, 1993 [JP] Japan .................................. 5-302385
Jun. 6, 1994 [JP] Japan .................................. 6-147061

[51] Int. Cl.$^6$ .......................... C09K 11/06; C07C 211/33
[52] U.S. Cl. ............................ 252/301.16; 252/301.22; 436/546; 436/800; 564/8
[58] Field of Search ................... 252/301.16, 301.22; 436/546, 800; 564/8

[56] References Cited

U.S. PATENT DOCUMENTS 4,659,817  4/1987  Gallop et al. ............................ 564/8

OTHER PUBLICATIONS

James et al., Journal of the Chemical Society, "Novel Photoinduced Electron–transfer Sensor for Saccharides based on the Interation of Boronic Acid and Amine", pp. 477–478 No. 4 Feb. 21, 1994.

James et al., Angewandte Chemie, "A Glucose–Selective Molecular Fluorescence Sensor", pp. 2207–2209 Nov. 1994.

*Primary Examiner*—C. Melissa Bonner
*Attorney, Agent, or Firm*—Wenderoth, Lind & Ponack

[57] ABSTRACT

Disclosed is a fluorescent compound of a molecular structure comprising a fluorophore, at least one phenylboronic acid moiety, and at least one amine-providing nitrogen atom where the nitrogen atom is disposed in the vicinity of the phenylboronic acid moiety so as to interact intermolecularly with the boronic acid. The compound emits fluorescence of a high intensity upon binding to saccharide(s), and is therefore suitable for use in the detection of saccharide(s).

6 Claims, 4 Drawing Sheets

FLUORESCENT COMPOUND SUITABLE FOR USE IN THE DETECTION OF SACCHARIDES

FIELD OF THE INVENTION

The present invention relates to a novel fluorescent compound, and particularly, to a fluorescent compound suitable for use in the detection of saccharides or sugars such as glucose, and to saccharide-detection with such fluorescent compound.

THE PRIOR ART

Saccharides or sugars are organic compounds indispensable to living organisms and play important roles in information transmission, energy metabolism and structure formation in such organisms. For example, glucose, more particularly, D-glucose, is crucial as an energy source for a variety of cells in constructing various organs. Glucose is stored in the liver as glycogen, which is released in body fluids as needed for energy consumption. The production and the consumption of glucose are well balanced in the body fluids of a normal or healthy human being, maintaining the glucose concentration in the fluids constant. Thus, the detection of glucose in the blood or the urine provides valuable information for the diagnosis of such diseases as diabetes and adrenal insufficiency.

Glucose sensor using an enzyme is the best known practical measure for detecting saccharides. This technique includes decomposing glucose with the enzyme (glucose oxydase), and measuring the amount of hydrogen peroxide produced by the decomposition through an appropriate means (such as by an electrode). While this method is an established one, the enzyme, which originates from a living body, will irreversibly change in quality as time elapses and cannot be recycled for repeated use. The sample cannot be provided for other purposes of measurement as the glucose has already been decomposed. In addition, the conventional sensor is directed to the detection of the sugar only in an in vitro sample, i.e. a sample taken out of the living body. If it should be possible to detect saccharides at sites inside the living body, there would be obtained much information very useful for the diagnosis and treatment of diseases and the development of medicines. However, the current saccharide sensor is far from meeting such expectations.

SUMMARY OF THE INVENTION

The present invention provides a novel fluorescent compound which, among various possible uses, is particularly suitable for use in the detection of saccharides. Thus, according to the present invention, there is provided a compound which is capable of emitting fluorescence by combining with saccharides, said compound having a molecular structure comprising a fluorophore, at least one phenylboronic acid moiety, and at least one amine-providing nitrogen atom where the nitrogen atom is disposed in the vicinity of the phenylboronic acid moiety so as to interact intermolecularly with the boronic acid.

A typical compound falling within such structure defined by the present invention can be expressed by the following general formula (1):

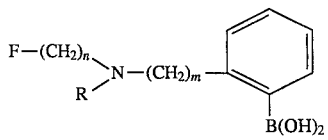

(1)

In the above formula (1), F represents a fluorophore. Examples of the fluorophore include a number of atomic groups or functional groups containing π-electron systems. Preferred fluorophores include naphtyl, anthryl, pyrenyl and phenanthryl, which can be expressed by the following structural formulas (2), (3), (4) and (5), respectively.

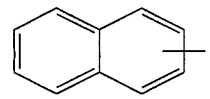

(2)

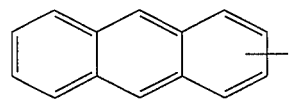

(3)

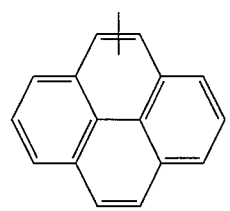

(4)

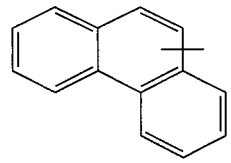

(5)

The fluorophore-forming atomic or functional groups can be substituted ones as long as the substituent(s) do not adversely affect the fluorescence. For example, the substitution with sulfonic acid group(s) is preferable, particularly when the compound is to be dissolved in an aqueous fluid for the detection of saccharides contained therein, as it imparts the compound with water-solubility. The most preferred fluorophore is exemplified by anthryl.

In the formula (1), R, combined with the nitrogen atom, denotes a lower aliphatic or aromatic functional group. In general R is an alkyl group having 1 to 4 carbon atoms, i.e. methyl, ethyl, propyl or butyl, or phenyl group.

In the formula (1), m is 0, 1 or 2. Thus the nitrogen atom in the compound of the present invention is disposed in the vicinity of the boronic acid moiety and the nitrogen atom is combined, through methylene group or ethylene group or directly, at the ortho position of the phenylboronic acid. Preferably m is i and thus the nitrogen is combined with the phenyl group through a methylene group.

In the formula (1), n is also 0, 1 or 2 where n+m is an integer of 2 or 3. Thus the nitrogen atom and the boronic acid are positioned not so far from the fluorophore. Preferably n is 1.

The phenyl group composing the phenylboronic acid may be substituted with an appropriate substituent or substituents as long as such substitution does not adversely affect the fluorescence. Examples of substituents are methyl, ethyl, propyl, butyl, phenyl, methoxy, ethoxy, butoxy and phenoxy groups.

The compound of the present invention as expressed by the formula (1) contains a fluorophore in its molecular structure but does not emit fluorescence in the absence of saccharides. It is understood this is because the fluorescence of the fluorophore is quenched by the unshared electron pair of the nitrogen atom: The electron of the nitrogen occupies the lowest excited singlet energy state of the fluorophore so as to supress the fluorescence. However, the compound of the present invention emits fluorescence of a high intensity, upon binding to saccharides. This phenomena can be accounted for as follows: The presence of saccharides produces a bond between the nitrogen atom(N) and the boron atom(B) to form a strong complex of the saccharide with the phenylboronic acid compound of the present invention, where the electron deficient boron atom has bound to the electron rich nitrogen. Thus, the unshared electron pair of the nitrogen atom will be utilized for bonding with the boron atom and will not contribute to the fluorescence-quenching electrogen transfer process, thereby expressing the intrinsic fluorescence of the compound.

A typical compound falling within the formula (1) of the present invention is the following compound of the formula (6), where F (the fluorphore) is anthryl, R is methyl and each of n and m is 1.

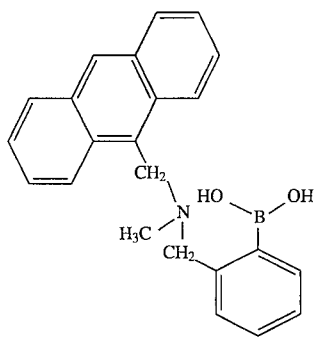

(6)

This compound features fluorescence of a highly increased intensity in the presence of monosaccharides, such as D-glucose and D-fructose. Thus, the compound is suitable for use in the detection of monosaccharides in general or even a specific monosaccharide. In the detection of a specific monosaccharide from a sample which may contain plural monosaccharides, the sample is generally subject to a pretreatment (e.g. a chromatography) for the separation of the monosaccharides, followed by the detection with the fluorescent compound of the present invention.

The detection with the fluorescent compound of the present invention is performed by adding the compound to the sample and by a photoscopic method, determining the increased intensity of the fluorescence due to the binding of the compound with the saccharide. Alternatively, the detection with the fluorescent compound of the present invention may be conducted by a chromatographic method where the compound of the present invention is supported on a supporting material through which the saccharide-containing sample is passed for the detection based on the increased fluorescent intensity due to the complex of the compound and the saccharide.

In accordance with the concept of the present invention there can also be provided a compound which may selectively bind to a specific saccharide thereby producing a highly increased fluorescence. In particular the present invention provides a fluorescent compound having the following general formula (7):

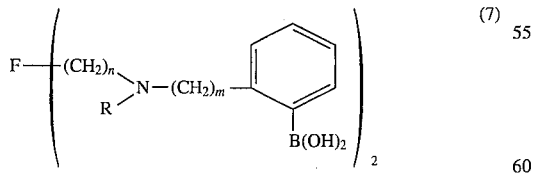

(7)

In the above formula, n and m each denote 0, 1 or 2 with n+m being 2 or 3, F represents a fluorophore and R represents a lower aliphatic or aromatic functional group.

The compound of the formula (7) is characterized by its selective binding to glucose resulting in a strong fluorescence. The compound is therefore suitable for use in the detection of glucose.

In the formula (7), n and m each denote an integer, with n+m being 2 or 3. Either of n and m may be zero; thus n and m each denote 0, 1, 2 or 3. Preferably n+m is 2 where each of n and m is 0, 1 or 2, with both of n and m most preferably being 1. Such specific length of the methylene($CH_2$) moiety of the compound of the present invention expressed by the formula (7) provides a molecular structure adapted to bind to glucose through the two boronic acid moieties of the compound.

In the formula (7), the fluorophores are exemplified by a number of atomic groups or functional groups containing $\pi$-electron systems. As preferred fluorophores are included naphthyl, anthryl, pyrenyl and phenanthryl, which can be expressed by the aforesaid structural formulas (2), (3), (4) and (5), respectively.

The fluorophore-forming atomic or functional groups can be substituted ones as long as the substituent(s) will not adversely affect the fluorescence. For example, the substitution with sulfonic acid group(s) is preferable as it imparts the compound with water-solubility. The most preferred fluorophore is exemplified by anthryl.

In the formula (7), R, combined with the nitrogen atom, denotes a lower aliphatic or aromatic functional group. In general R is an alkyl group having i to 4 carbon atoms, i.e. methyl, ethyl, propyl or butyl, or phenyl group.

Preferred compounds of the present invention failing within the formula (7) are exemplified by the following compounds (8), (9), (10) and (11), of which the compound (8) is particularly preferable.

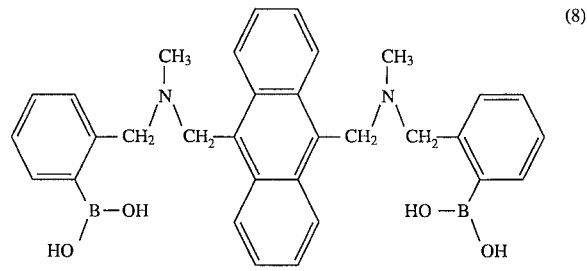

(8)

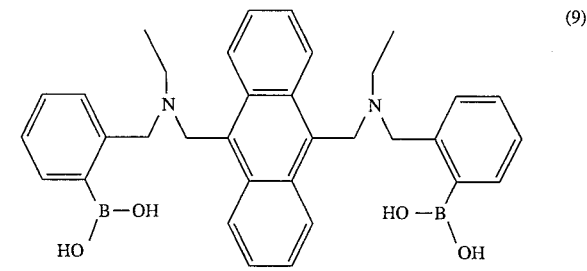

(9)

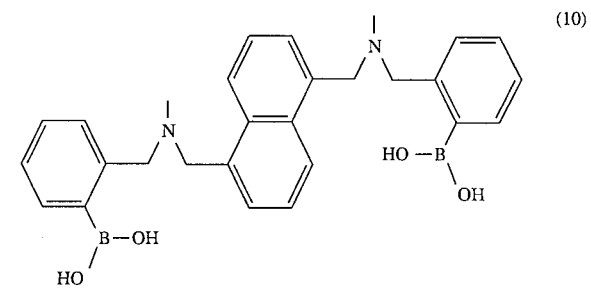

(10)

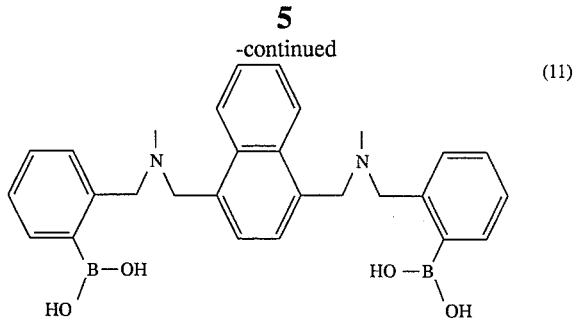

(11)

Surprisingly the compounds of the present invention, as typified by the compound (8), emit a strong fluorescence particularly in the presence of glucose in an aqueous solution of a concentration corresponding to those found in human body fluids(50–250mg/l or 0.0005M–0.0001M) and with a pH value of neutrality or near neutrality. Such strong fluorescence intensity does not change even in the coexistence with other saccharides such as galactose or fructose.

The emission of the strong fluorescence by the compound (7) of the invention in the presence of glucose can be construed as follows: The two boronic acid moieties as arranged in the structure of the formula (7) are suitable to bind covalently to the four hydroxyl groups (OH groups) at the 1, 2, 4 and 6 positions of glucose, thereby forming a stable 1:1 complex of the compound with glucose, in which the quenching by the nitrogen atom is assuredly prevented.

By contrast, other saccharides—such as fructose—may possibly bind only to one of the two boronic acid moieties, in which case there is observed only very weak fluorescence. In fact no substantial fluorescence can be observed by such saccharides as fructose or galactose in their concentrations as occurring in the human body fluids.

Thus, the compound of the present invention as typified by the formula (8) can emit a strong fluorescence specifically with glucose, due to the specific arrangement of the fluorophore, the two boronic acid moieties and the nitrogen atom, and therefore, is suitable for use in the detection of glucose. When the detection is made with a solution, the binding between glucose and the fluorescent compound can easily be cleaved by changing the pH of the solution through an appropriate acid, thereby restoring the glucose.

In general, the compound of the present invention can be prepared by allowing a phenylboronic acid having the ortho-position alkylhalogenated to react with a reagent composed of alkylaminomethyl group(s) bound to a fluorophore, in the present of a base under an appropriate solvent.

Through the application of the present invention saccharides such as glucose can be detected with very stable synthetic compound, in contrast to the conventional enzymatic method in which a rather unstable enzyme must be utilized for the detection of in glucose. Moreover, conducting the saccharide detection method with the compound of the present invention, a sample can be measured intact, i.e. without being decomposed as in the enzymatic method, and the sample can therefore be subjected to a further measurement or treatment.

The use of the compound of the present invention makes it possible to detect saccharide(s) by a spectroscopic means, without decomposing the saccharides. Thus, the technology has good prospects of developing into one in which the detection can be made in situ with respect to a specific region of an organ in the body. For example, by utilizing an optical fiber having the compound of the present invention coated on the tip thereof, the information on saccharide inside the body can be continuously monitored so as to provide useful clinical data.

It is noted that, in some of the chemical structural formulae given here, carbon atoms and hydrogen atoms as in methyl or methylene groups are omitted as conventionally done.

The invention is illustrated by the following examples for further understanding thereof.

EXAMPLE 1

Figure 1:
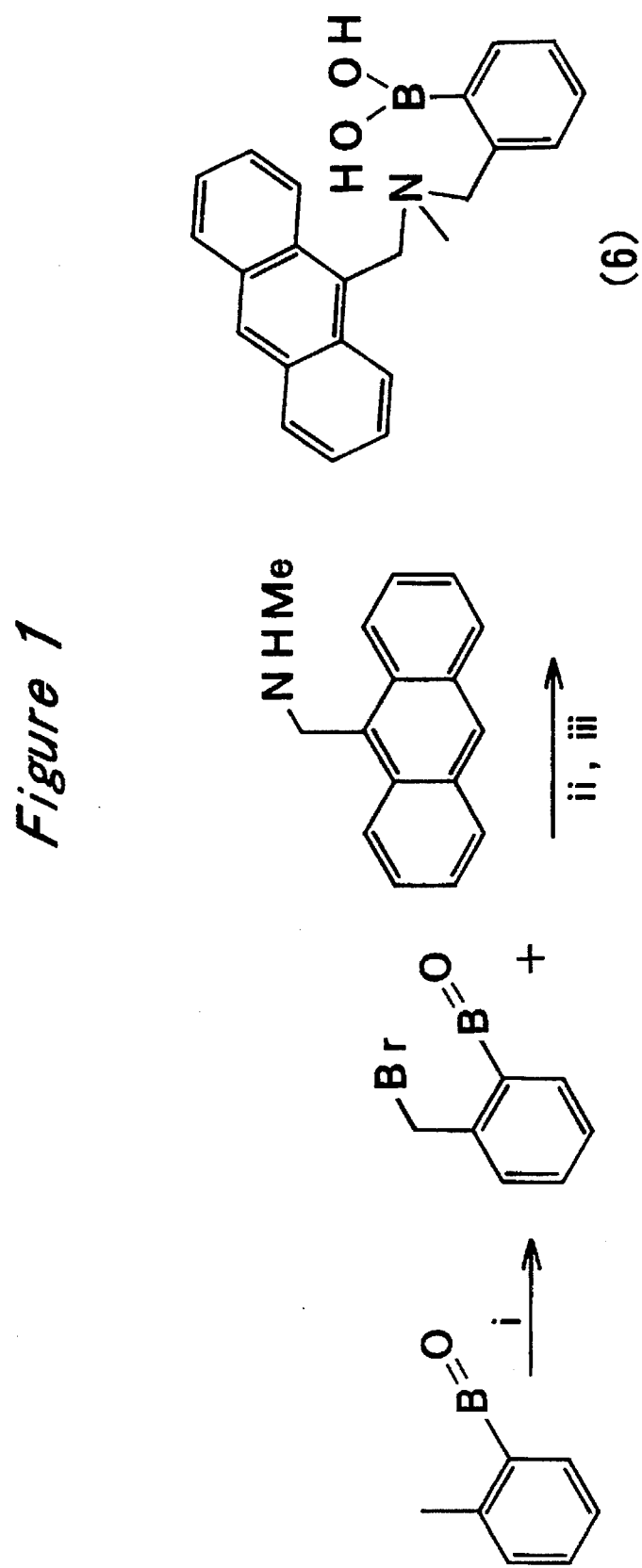
FIG. 1 is a scheme illustrating the synthesis of a fluorescent compound of the present invention.

The fluorescent compound of the formula (6) is prepared in accordance with the synthetic routes as shown in FIG. 1.

Firstly the phenylboronic acid is prepared as follows: Orthobromotoluene is reacted with magnesium (1.1 equivalents) in diethylether at 25° C. The Grignard reagent is added dropwise to a solution of trimethylborate (10 equivalents) in diethylether at −78° C. The mixture is stirred further 2 hours then allowed to warm to room temperature, and stirred further 2 hours. The diethylether is removed under reduced pressure, and the solid recrystallized from water. The product is boronic acid dried in a vacuum oven overnight.

The boronic anhydride is mixed with NBS (N-bromosuccinimide) (1.1 equivalents) and catalytic AIBN (azoisobutylnitrile) in carbonetetrachloride as solvent. The mixture is refluxed under radiation by a 200 W lamp for 2 hours. The solution is filtered when hot and the solvent removed to yeild the desired bromomethylboronic anhydride.

The bromomethylboronic anhydride is mixed with 9-metylaminomethylanthracene (2.1 equivalents) in chloroform and refluxed for 2 hours. The mixture is filtered when cool and the solvent is removed. The solid is then washed with diethylether and recrystallized from ethyl acetate, to give the desired product.

Analysis of the product: PMR (CDCl$_3$): chemical shift (ppm) 2.2 (3H, s), 3.9 (2H, s), 4.5 (2H, s), 7.4 (4H, m), 8.0 (4H, m), 8.4 (1H, s). MS (SIMS negative): mass plus glycol minus 2 waters and 1 proton 410.

EXAMPLE 2

The compound of the formula (6) as prepared in Example 1 is measured for fluorescence in order to evaluate the applicability of the compound to saccharide detection.

Arm aqueous solution of the compound (1.2×10$^{-5}$M) is prepared containing sodium chloride (0.05M). To the solution is added a saccharide (D-glucose or D-fructose) in a concentration of 0.05M to make the total volume of the resulting mixture 100 ml. The measurements are carried out by varying the pH from approx. 12 by the stepwise addition of HCl. The sample taken out the solution is subject to the measurement of fluorescence spectrum after the pH value is stabilized and then returned to the solution, followed by the addition of HCl to adjust the pH for further measurement. The fluorescence spectra are measured on a Hitachi Fluorophotospectrometer F-4500, in which UV is utilized for the excitation. The results are shown in FIG. 2.

Figure 2:
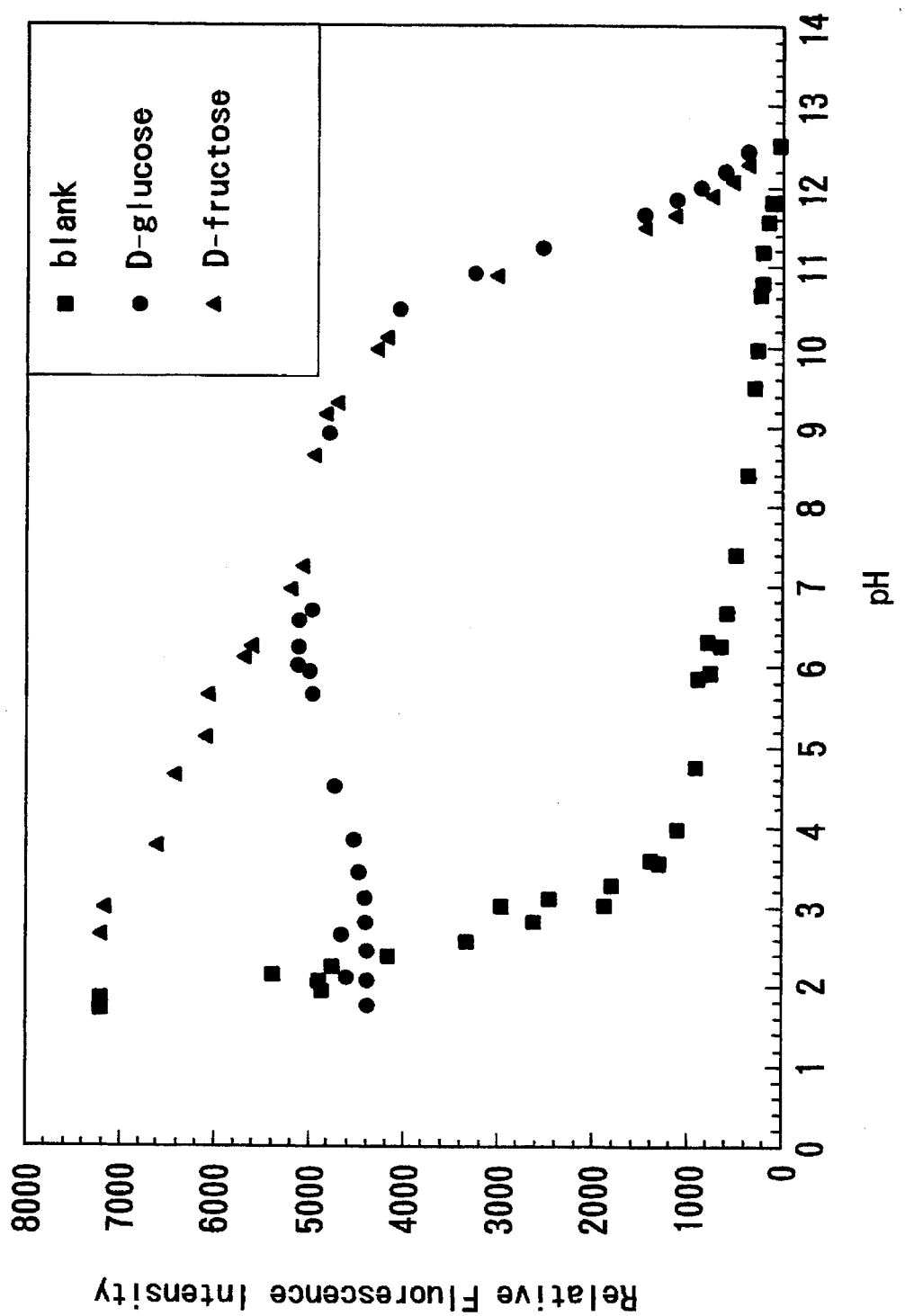
FIG. 2 demonstrates fluorescence intensities of the compound of the invention in the presence of monosaccharides.

As can be seen from FIG. 2, the compound of (6) is very low in fluorescence intensity over the pH range from about 3 to the higher pH, suggesting that the fluorescence due to anthracene is quenched. However, in the presence of the saccharides, the fluorescence is highly increased over a wide pH range of 4 to 10. It is therefore understood that the compound (6) can be used in the detection of saccharides through fluorescence.

EXAMPLE 3

Figure 3:
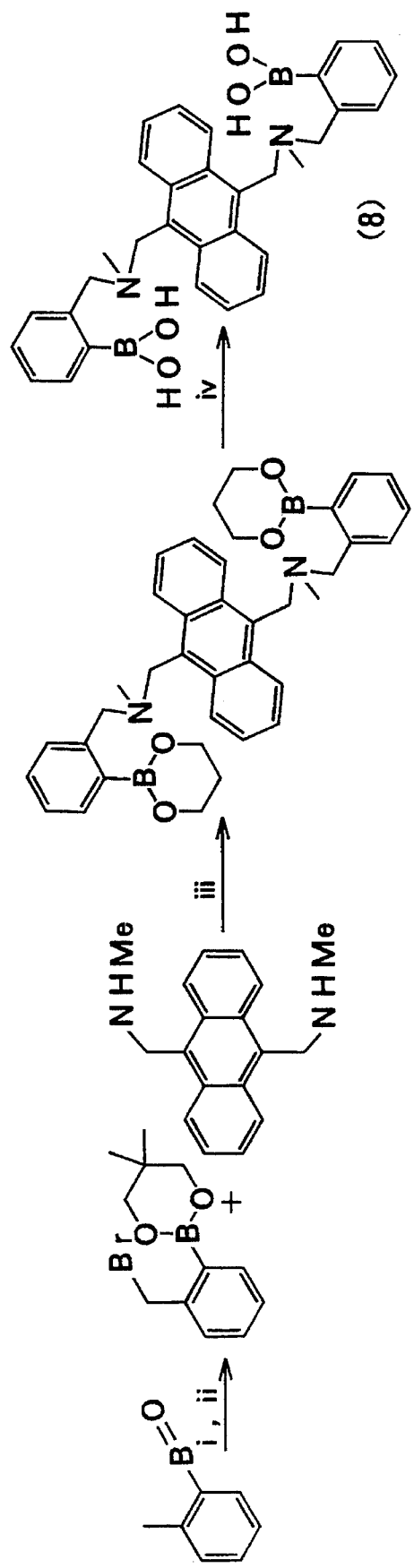
FIG. 3 is a scheme illustrating the synthesis of another fluorescent compound of the present invention.

The fluorescent compound of the formula (8) is prepared under the synthetic routes as shown in FIG. 3.

The orthomethyl boronic acid is bromiated with NBS in carbon tetrachloride with AIBN as initiator under reflux and lighting for 3 hours (Yield 60%) (i). The resulting ortho-bromomethyl boronic acid is then reacted with 2,2-dimethyl-1,3-propanediol in toluene with azeotropic removal of water overnight (Dean-Stark) (Yield quantitative) (ii).

The protected orthobromomethyl boronic acid is then reacted with the anthryl diamine and potassium carbonate in THF under reflux overnight (Yield 5% isolated) (iii).

The protecting group is removed in 33.3% MeOH/H2O at pH 7.77 and room temperature (iv).

Analysis of the product (protected diboronic acid): PMR (CDCl$_3$, 300 MHz): chemical shift(ppm) 7.2–8.4(m, aromatic, 16H), 4.4(s, CH$_2$(anthrylic), 4H), 3.9(s, CH$_2$(benzylic), 4H), 3.6(s, CH$_2$(protecting group), 8H), 2.2(s, CH$_3$N, 6H), 0.9(s, CH$_3$(protecting group), 12H). MS (SIMS: NPOE): mass plus 668.

EXAMPLE 4

The compound of the formula (8) as prepared in Example 3 is measured for fluorescence in order to evaluate the applicability of the compound to glucose detection.

The diboronic acid compound (8) is dissolved in buffered (pH7.77, 0.01M KCl, 0. 00262M KH$_2$PO$_3$ and 0.002642M Na$_3$HPO$_3$) methanolic aqueous solution (33% methanol in water). Portions of saccharide are added into 100 ml of the solution and the fluorescence spactra are measured on a Hitachi F-4500 Fluorospectrophotometer with a Hewlett Packard VETRA 286/12 computer. UV (370nm) is utilized for the excitation.

Figure 4:
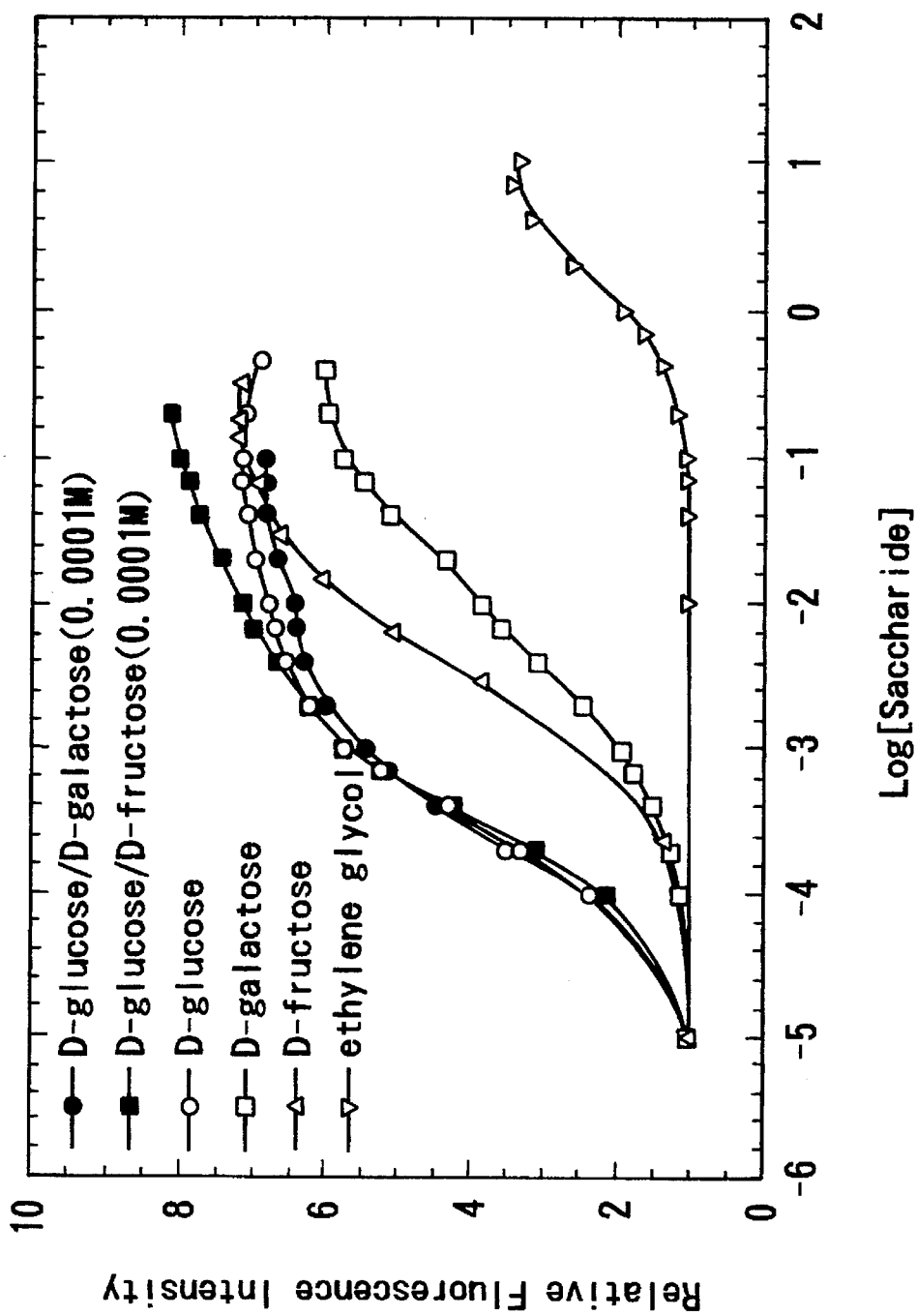
FIG. 4 demonstrates fluorescence intensities of the compound of the present invention in the presence of glucose and other monosaccharides.

The results are shown in FIG. 4, in which the abcissia represents logarithmic molar concentration of saccharide and the ordinate denotes relative fluorescence intensity. As can be seen from the figure, the compound (8) of the present invention emits a strong fluorescence particularly in the presence of glucose even in a relatively small concentration. It is particularly noted that the fluorescence intensity increases linearly with the saccharide concentration, in the range of 0.0005M to 0.001M corresponding to the glucose concentration normally to be measured in human body fluids. This trend holds not only in the case of the presence of glucose alone but also in the case of the presence of glucose concurrently with other saccharides such as galactose or fructose.

By contrast, the compound (8) develops almost no fluorescence in the presence of ethyleneglycol as control. With respect to galactose or fructose the compound does not exhibit any substantial fluorescence even in the maximum possible concentration of such saccharide in the body fluids (0.0001M), but develops the fluorescence only when the concentration of such saccharide is higher by one or two orders of magnitude. It is therefore understood that the compound (8) of the present invention can be used in the detection of glucose as it emits strong fluorescence particularly in the presence of glucose.

What is claimed is:

1. A fluorescent compound of the following general formula:

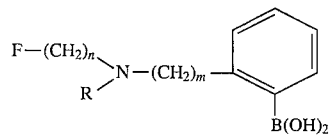

in which F represents a fluorophore, R is selected from the group consisting of lower aliphatic and aromatic functional groups, and n and m each is 0, 1 or 2 with n+m being 2 or 3.

2. A fluorescent compound as claimed in claim 1 in which F is selected from the group consisting of naphtyl, anthryl, pyrenyl and phenanthryl.

3. A fluorescent compound of the following formula

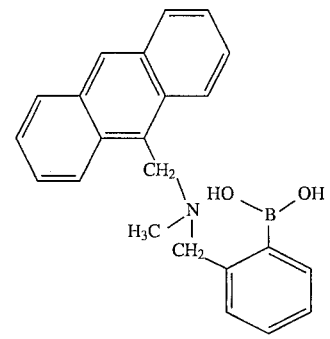

4. A fluorescent compound of the following general formula:

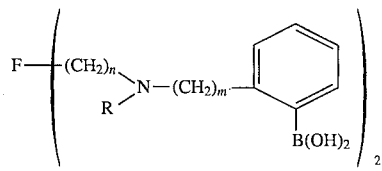

in which F represents a fluorophore, R is selected from the group consisting of lower alliphatic and aromatic functional groups, and n and m each is 0, 1 or 2 with n+m being 2 or 3.

5. A fluorescent compound as claimed in claim 4, in which F is selected from the group consisting of naphtyl, anthryl, pyrenyl and phenanthryl.

6. A fluorescent compound of the following formula

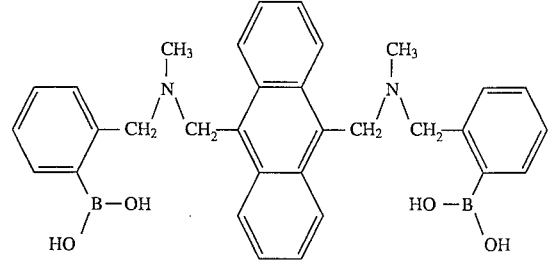

* * * * *